United States Patent
Kozhemiakin et al.

[11] Patent Number: 6,122,550
[45] Date of Patent: Sep. 19, 2000

[54] DEVICE FOR THERAPEUTIC ACTION ON HUMAN ORGANISM

[76] Inventors: Alexander Kozhemiakin, per. Urtochni 18, Tomsk; Alexander Spiridonov, ul Kropotkina 134-110, Novosibirsk; Leonid Matusis, ul. Belinskogo 1066-143, Niznii Novgorod; Eduard Yashin, Zelinograd 505-11, Moscow, all of Russian Federation

[21] Appl. No.: 09/019,596

[22] Filed: Feb. 6, 1998

[51] Int. Cl.$^7$ ........................................ A61F 2/00
[52] U.S. Cl. ........................ 607/101; 607/100; 607/113
[58] Field of Search ............... 604/890.1, 891.1, 604/19, 20; 607/1, 2, 35–37, 59, 60, 96, 100, 101, 113, 115, 154–156; 128/897, 898, 899, 903

[56] References Cited

U.S. PATENT DOCUMENTS

| | | | |
|---|---|---|---|
| 3,077,195 | 2/1963 | Folsche | 607/101 |
| 5,315,994 | 5/1994 | Guibert et al. | 607/101 |
| 5,626,630 | 5/1997 | Markowitz et al. | 607/60 |
| 5,814,089 | 9/1998 | Stokes et al. | 607/60 |
| 5,842,977 | 12/1998 | Lesho et al. | 600/300 |

FOREIGN PATENT DOCUMENTS

| | | |
|---|---|---|
| 2008040 | of 0000 | Russian Federation . |
| 2040928 | of 0000 | Russian Federation . |
| 1341762 | of 0000 | U.S.S.R. . |
| 1588416 | of 0000 | U.S.S.R. . |
| 1697850 | of 0000 | U.S.S.R. . |
| 1703103 | of 0000 | U.S.S.R. . |

OTHER PUBLICATIONS

V.H. Volchenko "Methodology of Acupuncture Action of Electromagnetic Radiation of MM Range for Regulating Human Condition", M. Ipe An USSR, 1987.

N.D. Kalbun "Bionic Modeling of Operator Action in MM–Range of Wavelength", Electronic Industry, 1991, No. 5, pp. 43–44.

*Primary Examiner*—Michael Peffley
*Assistant Examiner*—Bryan K. Yarnell
*Attorney, Agent, or Firm*—I. Zborovsky

[57] ABSTRACT

A device for therapeutic action on a human organism has a hermetically closed housing composed of a material which is transparent for extra high frequency radiation, a generator accommodated in the housing and generating extra high frequency radiation in the range of 36–78 GHz, and a modulator modulating the radiation which is generated by the generator with a frequency of a low frequency in the range of 0.1–9.8 Hz so as to provide a resulting radiation which is specific for a corresponding pathology of the human organism.

9 Claims, 2 Drawing Sheets

DEVICE FOR THERAPEUTIC ACTION ON HUMAN ORGANISM

BACKGROUND OF THE INVENTION

The present invention relates to devices for therapeutic action on human organism. More particularly it relates to devices which utilize short wave frequency therapy which is used in reflexology and physiotherapy.

Short wave frequency therapy is used for treating many diseases. Some of the devices for such therapy are disclosed in the inventor's certificate of the Soviet Union 1,588,416 and Russian patents 2,008,040; 2,040,928 and in Russian patent application no. 96101587/14. These devices include a generator on a semi-conductive diode, an irradiator adjoining the generator and a power source. The generator operates on predetermined physiologically active frequency with deviation of 50–100 Mhz from carrying frequency. Other devices are disclosed in the inventor's certificate of the Soviet Union 1,697,850; 1,341,762; 1,703,103. Further devices are disclosed in the publications: V. H. Volchenko, et al "Methodology of Acupuncture Action of Electromagnetic Radiation of MM-Range for Regulating Human Condition" M. Ipe An USSR, 1987; and N. D. Kolbun "Bionic Modeling of Operator Action in MM-Range of Wavelength", Electronic Industry, 1991, No. 5, pages 43–44. Some devices are also produced and utilized in practical medicine in the Russian Federation.

The most efficient electromagnetic irradiation has been executed in a millimeter range, in particular with the frequency of 36–78 GHz generated by a specific source. The known devices for the electromagnetic irradiation are usually stationary devices operating at certain frequencies. One disadvantages of the existing devices is .that they are not sufficiently specific for each case or each pathological, and therefore first of all they can act simultaneously on pathological and healthy cells which is a highly undesirable, and also do not provide an optimal dosage of action on the pathological cells. In addition, the existing devices are stationary devices which can be used in hospitals provided with the corresponding equipment, but they are not designed to be used by patient's at home.

SUMMARY OF THE INVENTION

Accordingly, it is an object of present invention to provide a device for electromagnetic irradiation of human organism, which avoids the disadvantages of the prior art.

In keeping with these objects and with others which will become apparent hereinafter, one feature of present invention resides, briefly stated, in a device for therapeutic action on a human organism, which has a hermetically closed housing which is preferably formed as a body of revolution of oval shape composed of a material which is transparent for electromagnetic irradiation in a short frequency range, a generator for generating electromagnetic irradiation within this range, and a modulator which modulates the generated radiation so as to more specifically adjust the radiation to a pathology to be acted upon by the device.

The increased efficiency of therapeutic action with the inventive device when compared with known devices is obtained first of all because in it a combination of two treatment factors is provided, with extra high frequency EHF and low frequency LF. In other words. the millimeter range of frequencies or EHF is modulated LF.

Therapeutic action of low frequency range is widely used. The generation of the frequencies is performed by means of electropunctual therapy. For a great number of pathologies, in particular within the range of low frequencies the most suitable fixed therapeutic frequencies are determined. However, in addition to the fact that the mechanism of their therapeutic action is different in principle from the therapeutic action of the extra high frequencies, they are insufficiently efficient for various pathologies. Their action on natural inner cavities of organism is not possible, and also they do not provide a contact action.

When in accordance with the present invention there is a combined therapeutic action of the extra high frequency and low frequency range, it is possible to provide efficient therapeutic action of many pathologies with the use of designs utilized in the present invention.

When the device is designed in accordance with the present invention, it eliminates the disadvantages of the prior art and provides for an accurately adjustable and specifically targeted radiation to be used for irradiation corresponding parts, organs, cells of the human organism.

In accordance with another embodiment of the present invention, the device can have a housing composed of a radiation-transparent material, and a generator of radiation accommodated in the housing, so that the pill can be attached to a patient's body, for example by an adhesive tape, with a radiating side of the generator facing the body. The modulator and the current source are arranged in this case in a separate casing which is connected with the generator by conductor.

In accordance with another embodiment of the invention, the device can have a single housing which accommodates the generator, as well as the modulator and the current source located inside the housing. In this case, the whole pill can be swallowed by a person, then the radiation is released inside the person, and after this the pill is evacuated from the organism in a natural way with the patient's stool.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

Figure 1:
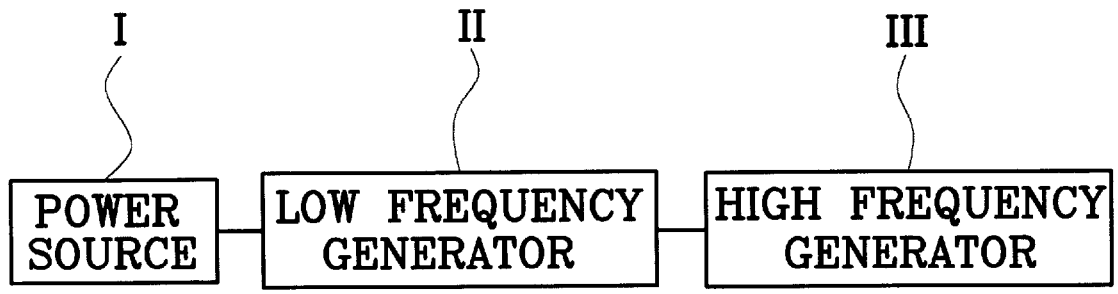
FIG. 1 is a schematic view showing a general circuitry for an inventive device for therapeutic action.

In accordance the present invention in the inventive device the curing factors of signals of extra high frequencies EHF in mm range and of extra low frequencies LF $10^{10}$–$10^{11}$ are utilized. As shown in FIG. 1 the device generally has a power source I, a generator of extra low frequency II, and a generator of extra high frequency III. Current from the power source is supplied to the generator II which generates pulses with a frequency of repetition corresponding to one of the therapeutic frequencies of P. Voll and with amplitude which is sufficient for supplying the generator III. The frequency of pulses of the generator II can be smoothly regulated so as to provide a desired therapeutic frequency, which is shown on an indicator. The pulse of the generator II provides a current supply for the generator III, which during the bandage of this pulse generates a therapeutic signal with the frequency component of extra low frequency and extra high frequency ranges. Then the resulting signal is applied to a patient's organism, or is supplied by means of an attachment which will be described hereinbelow into an inner cavity of the organism. In the device the autonomous power source can be utilized as well as the pulse generator of extra low frequency range formed as a quartz synthesizer of frequency with a pitch of its readjustment of 0.01 Hz and an indicator of frequency of pulse repetition on a liquid crystal display. The frequency of the pulses are adjusted within the range of 0.1–25 Hz. The time of the generated pulse was 1 microsecond, and the amplitude was 5 V which is necessary for operation of the generator III. The generator III was made on the basis of weak Gunn diode located in a resonator formed on the basis of planar transmission line. The generator III is mounted in a miniature hermitic polymer housing which is mounted to the patient's body or contactlessly irradiates a skin area, or by means of an inter cavity attachment acts on the corresponding zone. The output power of the generator III in the pulse was not more than 10 mwt as the therapeutic frequency 42.2 GHz, with the average not more than 1 mwt.

Figure 2:
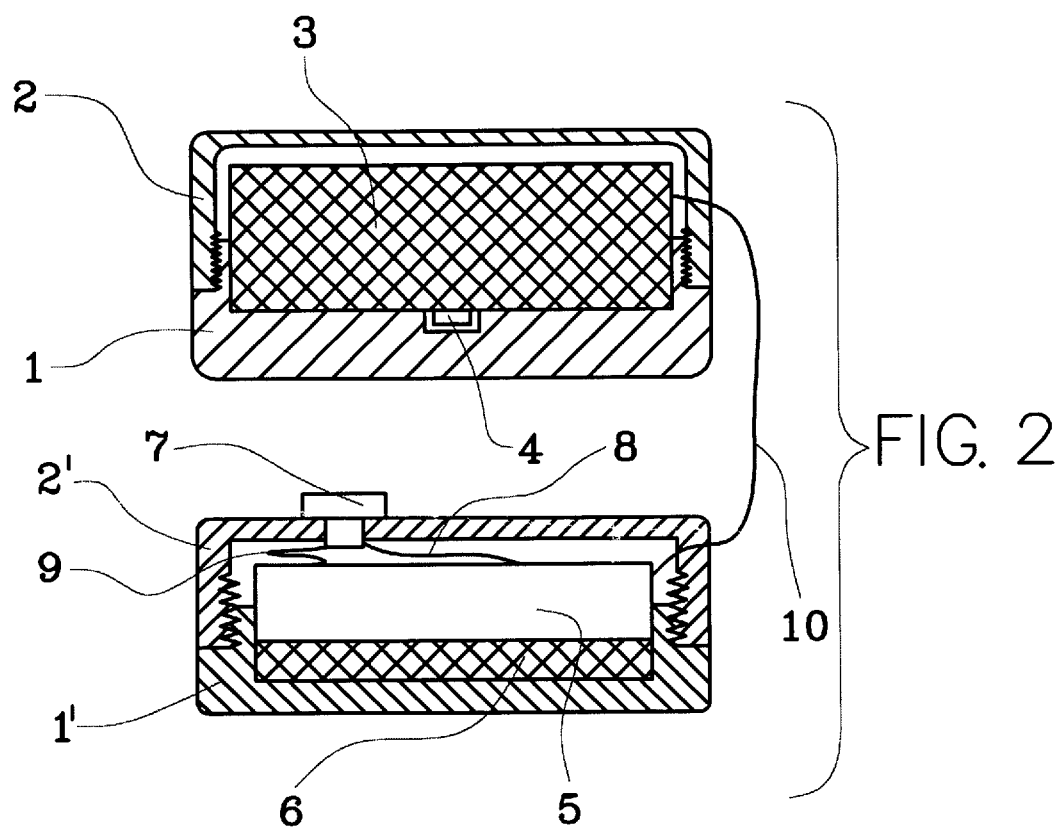
FIG. 2 is a view showing a device for therapeutic action in accordance with a first embodiment of the present invention.

In accordance with one embodiment of the present invention shown in FIG. 2, a device for therapeutic action on human organism has a housing. The housing is formed as a hermetically closed body of revolution which has an oval shape and composed of short wave frequency a radiation-transparent material, for example fluoroplastic which is allowed to be used in medicine. With the above described shape, the device resembles a conventional pill. In the embodiment shown in FIG. 2, the housing includes a base 1 and a cover 2 which are connected with one another, for example by thread. A generator of radiation 3, preferably in a hybird form is arranged inside the housing and provided with a generator diode 4. The device can have another housing which includes another base 1' and another cover 2' connected with the base 1' for example by a thread. A battery 5 together with a modulator 6 are accommodated in the housing 1', 2'. Also, a microswitch 7 is provided in the housing 1', 2' as well as a springy conductor 8 and a supply conductor 9. A conductor 10 connects the current supply source with the generator.

The device, in particular the housing 1, 2 with the generator 3 and the generator diode 4 during the operation can be attached to a patient's body for example by an adhesive layer, etc. provided on the housing. The generator generates an electromagnetic radiation in a millimeter range at the frequency of 36–78 GHz, while the modular modulates this frequency with frequencies which are specific for each pathology, in particular from 0.1 to 9.8 Hz, with the accuracy of 0.01 Hz. The device therefore operates with high efficiency, with the irradiation specifically adjusted in accordance with the specific pathology, in complete aseptic conditions, without invasiveness, pain and discomfort.

Figure 3:
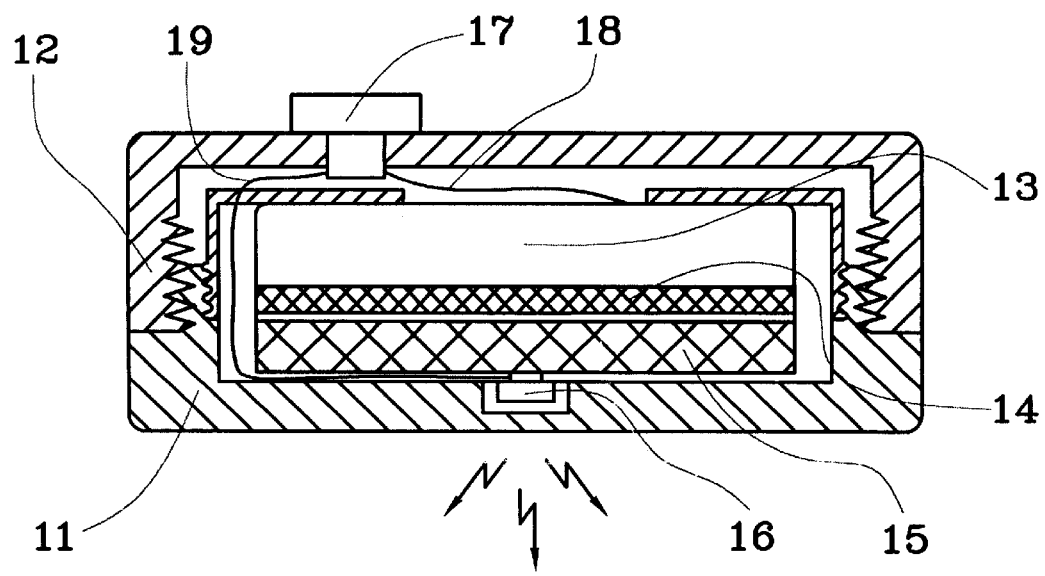
FIG. 3 is a view showing the inventive device in accordance with another embodiment.

In accordance with a further embodiment of the present invention shown in FIG. 3. In this embodiment shown in FIG. 3, the device can also be formed as a pill having a housing composed of radiation transparent material, for example a fluoroplastic and including a base 11 and a cover 12 connected with a base by a thread. A current supply such as a battery 13 is arranged inside the housing. Reference numeral 14 identifies a modulator, while reference numeral 15 identifies a generator preferably in a hybrid form and provided with a generator diode 16. The device has a microswitch 17, a springy conductor 18 and a supply conductor 19. The device is formed also as a pill. However, in contrast to the device shown in FIG. 2, all elements of the device are accommodated in a single housing or in a single pill. The device in accordance with the embodiment shown in FIG. 3 can be swallowed by a patient, then it releases radiation inside the patient to act on a corresponding body part, organ, or cells, and then it is naturally evacuated with the patient's stool.

The operation of the device shown in FIG. 3 is substantially similar to the operation of the device shown in FIG. 2.

When the device is introduced into a current conductive medium, for example inside the organism during its swallowing or when it is accommodated in a cavity of the organism, the outer metallic contacts of the device are closed and the current is supplied to the generator, which, through the radiation transparent housing, irradiates a desired area.

The device has been tested on a group of ulcer-suffering patients. There were two groups each containing 19 patients. In a control group the treatment was performed in accordance with a known method, such as for example described in the publication "Microwave Resonance Therapy" by E. Kuropatov, N Novgorod, 1994. In another group the patients swallowed the proposed device, which then evacuated from the organism in a natural way. The efficiency of the treatment was determined by examination, inquiries and palpations, as well as endoscopic and x-ray tests seven days after the treatment.

The table presented hereinbelow illustrates the efficiency of the treatment.

|  | Stable Improvement | | Relative Improvement | | No Improvement | | Total | |
| --- | --- | --- | --- | --- | --- | --- | --- | --- |
|  | Number of Patients | | | | | | | |
|  | Abs | Rel | Abs | Rel | Abs | Rel | Abs | Rel |
| Therapy with old device | 8 | 42 | 8 | 42 | 3 | 16 | 19 | 100 |
| Therapy with new device | 10 | 53 | 8 | 42 | 1 | 5 | 19 | 100 |

It can be seen that new inventive device increases efficiency and reduces time of treatment.

Figure 4:
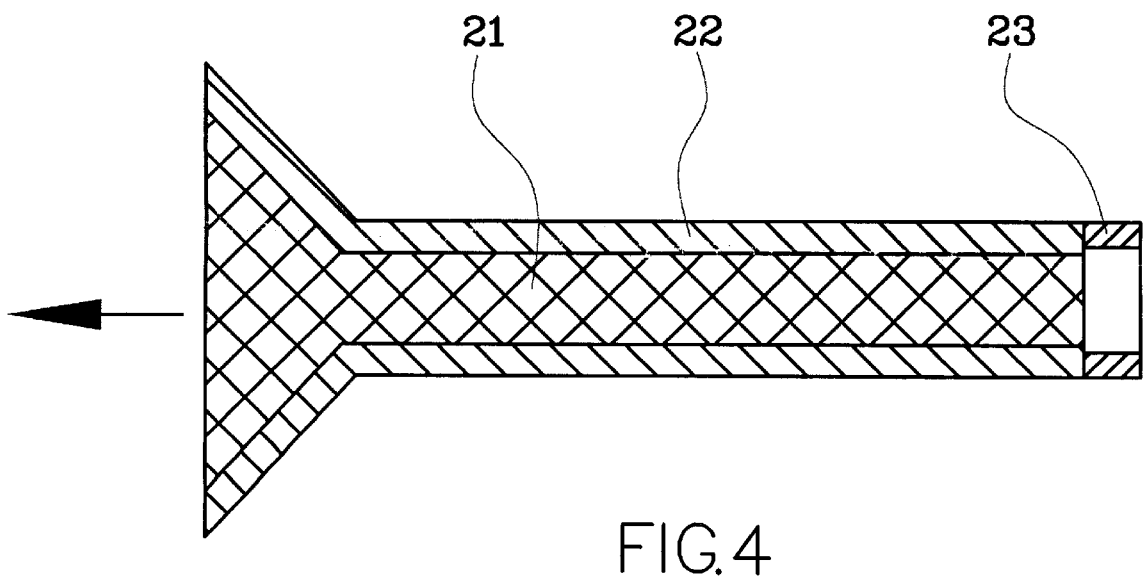
FIG. 4 is a view showing a replaceable attachment to be attached to the inventive device.

The device is provided with a plurality of attachments which can be introduced into any inner cavity of the organism for applying its action in a corresponding zone. The attachment shown in FIG. 4 includes a dielectric radio transparent core 21, a metal casing 22, and a mounting part 23. The attachments can have different sizes and constructions.

It will be understood that each of the elements described above, or two or more together, may also find a useful application in other types of constructions differing from the types described above.

While the invention has been illustrated and described as embodied in device for therapeutic action on human organism, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

What is claimed is:

1. A device for therapeutic action on a human organism, comprising a hermetically closed housing composed of a material which is transparent to extra high frequency radiation; a generator accommodated in the housing and generating extra high frequency radiation with therpautic Frequencies in the range of 36–78 GHz; and a modulator modulating the radiation which is generated by said generator with a frequency of a low frequency in the range 0.1–9.8 Hz so as to provide a resulting modulating thorpe radiation which is specific for a corresponding pathology of the human organism to form means for applying therapeutic action to the human organism with the modulated therapeutic radiation.

2. A device as defined in claim 1, wherein said housing is formed as a hollow body of revolution having an oval shape.

3. A device as defined in claim 2, wherein said housing is pill-shaped.

4. A device as defined in claim 1, and further comprising a separate housing which accommodates said modulator; and a conduit connecting said modulator with said generator.

5. A device as defined in claim 4, and further comprising a power supply arranged in said housing in which said modulator is accommodated.

6. A device as defined in claim 1, wherein said modulator is also accommodated in said housing.

7. A device as defined in claim 1, wherein said generator is provided with a generator diode.

8. A device as defined in claim 1; and further comprising a plurality of attachments insertable into body cavities for delivering the resulting radiation to a corresponding organ.

9. A device as defined in claim 1; and further comprising a power source accommodated in said housing.

* * * * *